United States Patent
Riek et al.

[19]

[11] Patent Number: 6,001,084

[45] Date of Patent: Dec. 14, 1999

[54] MEDICAL NEEDLE FOR ENDOSCOPIC SURGERY

[76] Inventors: Siegfried Riek, Konrad-Witz-Strasse 11, 78628 Rottweil; Karl-Heinz Bachmann, Fronwiesen 9; Thomas Gaiselmann, Teichwiesen 4, both of 78667 Villingendorf, all of Germany

[21] Appl. No.: 08/767,530

[22] Filed: Dec. 16, 1996

[30] Foreign Application Priority Data

Dec. 18, 1995 [DE] Germany .......................... 195 47 246

[51] Int. Cl.⁶ ...................................................... A61M 5/32
[52] U.S. Cl. ................................ 604/272; 604/264; 128/4
[58] Field of Search ................................ 604/272, 264, 604/280; 128/4–11; 606/167, 170, 172, 185

[56] References Cited

U.S. PATENT DOCUMENTS 4,354,762  10/1982  Yoon .
5,385,572  1/1995  Nobles et al. .

FOREIGN PATENT DOCUMENTS

| 0 642 764 | 11/1994 | European Pat. Off. . |
| 0 684 016 | 8/1995 | European Pat. Off. . |
| 1 616 107 | 4/1971 | Germany . |
| 91 12 976 U | 1/1991 | Germany . |
| 40 35 146 | 4/1992 | Germany . |
| WO 96/01132 | 6/1996 | WIPO . |

*Primary Examiner*—John D. Yasko
*Attorney, Agent, or Firm*—Irvin A. Lavine; Nath & Associates

[57] ABSTRACT

A medical needle for endoscopic surgery has an external cannula tube in which a protective element is mounted so that it can be shifted axially against a spring. The distal, front protective surface of the protective element in a forward position projects beyond the sharp tip of the cannula tube and in a rear position is behind this tip. The protective surface of the protective element is transparent and can be observed through an optical system installed in the protective element.

20 Claims, 2 Drawing Sheets

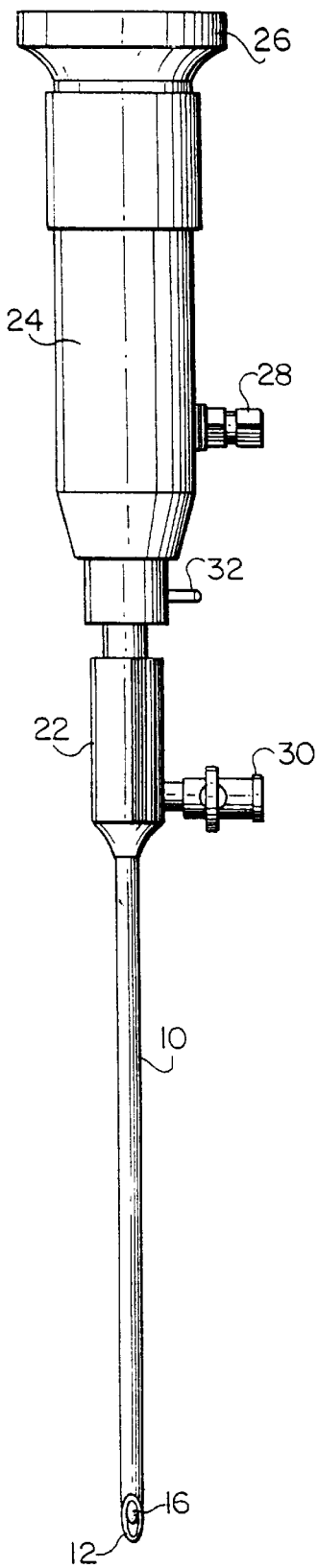
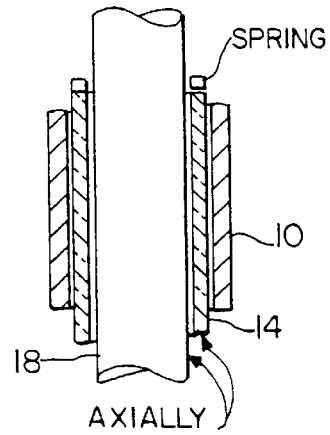
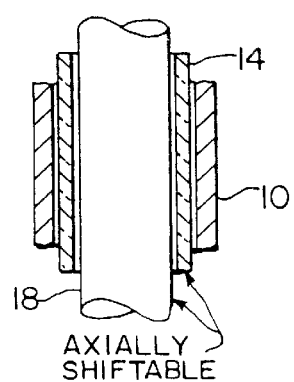
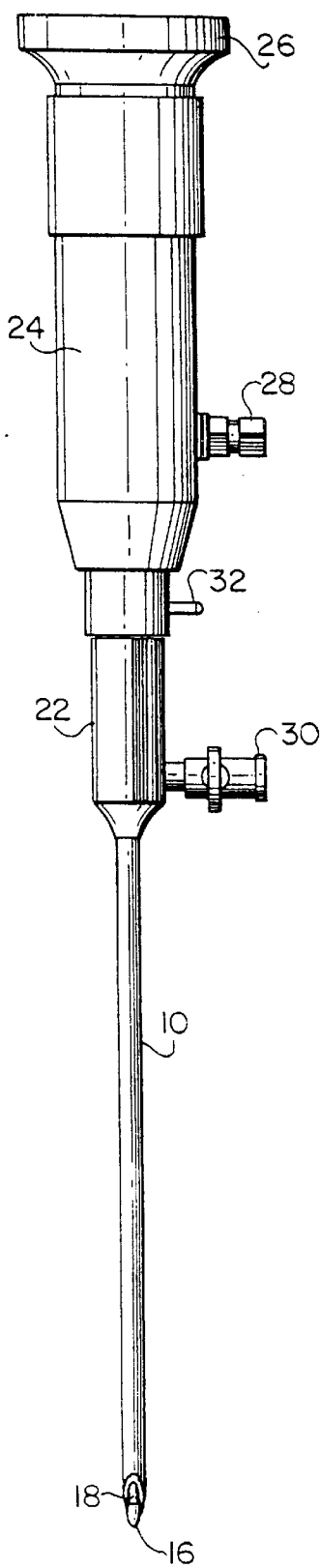
FIG. 1A
FIG. 1
FIG. 1B
FIG. 2

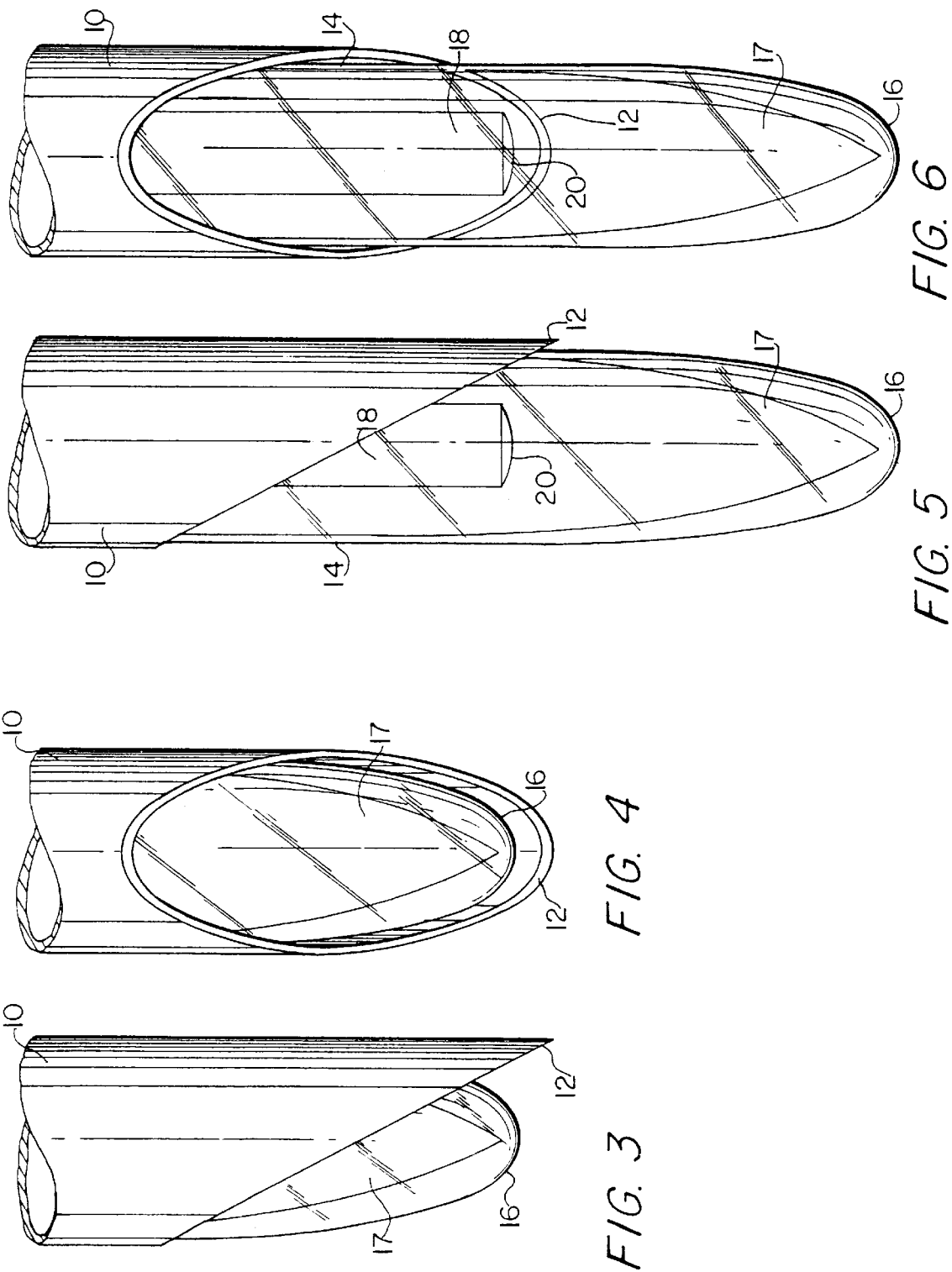

MEDICAL NEEDLE FOR ENDOSCOPIC SURGERY

FIELD OF THE INVENTION

The invention relates to a medical needle for penetrating the abdomen.

BACKGROUND OF THE INVENTION

In order to reduce the risk in endoscopic surgery of injury to blood vessels or internal organs through puncture, the so-called Veres needle is used. The Veres needle has a hollow outer cannula that is ground obliquely at its distal end to a sharp, penetrating point. A protective element is mounted in the cannula which can be shifted axially and is a spring element that has a closed, blunt, only slightly arched protective surface at its front, distal end. The protective element function as a tube for the insufflation of gas with an opening mounted on the side behind the distal tip.

The Veres needle preferably is used in endoscopic abdominal surgery to introduce pneumoperitoneum in the first puncture. For this, a small incision is first made in the skin, the Veres needle is then introduced into the subdermal fatty tissue, and the protective element is pressed distally forward through the force of the spring, because the resistance in the subdermal fatty tissue is less than the force of the spring. The blunt protective surface of the protective element projects distally forward over the sharp tip of the hollow cannula and displaces the subdermal fatty tissue bluntly, so that no vascular injuries occur in the subdermal fatty tissue due to the sharp, penetrating tip. If the fascia is reached, the resistance of the tissue increases greatly and becomes greater than the force of the spring that presses the protective element forward. The protective surface of the protective element recedes behind the sharp tip and the latter can now penetrate the fascia. Immediately after penetration of the fascia, the counterpressure of the tissue drops again, so that the force of the spring can then shift the protective element forward, and the protective surface protects the sharp tip in the area of the preperitoneum again. As soon as the peritoneum is reached, the pressure against the tip increases again so that the protective element with the protective surface again is pushed back and the sharp tip can open the peritoneum As soon as the tip slides forward into the abdominal cavity, the protective element again rushes forward under the force of the springs because the free abdominal cavity offers no resistance The blunt protective surface, therefore, protects the vessels and intestine in the free abdominal cavity from injury by the sharp tip.

With the Veres needle, the penetration of the fascia and the peritoneum is recognized in that the protective element is pushed backwards and after penetration again rushes forward. This known Veres needle also has a considerable residual risk. For example, intestinal loops adhering to the wall of the peritoneum and large vessels lying in the area of the retroperitoneum in certain circumstances may not be noticed, because the sharp tip, immediately after penetrating the peritoneum, penetrates these intestinal loops or vessels without the protective element being able to quickly move forward.

This residual risk is reduced by a needle of the nature of the generic terms as recognized in German No. 9,112,976 U1 and similarly in U.S. Pat. No. 4,254,762. In the case of this needle, the protective element that can be shifted in the cannula tube provided with the sharp tip is formed as a tube and has at its distal, front end a translucent, blunt protective surface An optical system is installed in the tubular protective element by which the protective surface can be observed from inside. The protective element, therefore, not only fulfills the function of protection as with the conventional Veres needle, but in addition, makes an optical observation of the tissue layers penetrated possible for the operator of the needle, and thus, the possibility of checking whether the free abdominal cavity is actually reached after penetration of the abdominal wall. In the case of this known needle, however, the distal protective surface of the protective element is constructed as an even front face running vertically to the axis of the cannula. If this even protective surface is applied to the tissue under the pressure of the force of the spring, the tissue will be pressed flat, so that no optical differentiation is then possible between fatty tissue, fascia, and muscle tissue Although this is to be prevented in that during the puncture, the flat protective surface moves back behind the sharp tip of the cannula tube, so that a free space remains between the tip and the protective surface, this free space fills with blood during the puncture, so that differentiating observation is also not improved in this manner.

Furthermore, a trocar is known, see German 4,035,146 C2 , whose penetrating tip is made as a transparent window. An optical system inserted into the trocar shaft allows observation both of the tissue lying directly in front of the tip as well as of the tissue lying to the side of the tip when the trocar tip penetrates. The operator, therefore, can penetrate the tissue in view. This trocar, however, has a relatively large external diameter. In the case of thin needles of only 2–3 mm external diameter, it is difficult to produce a transparent tip with the mechanical properties required for the penetration.

From EP 0,684,016 A2 and EP 0,642,764 A1, a trocar is known in which the distal tip is rounded and transparent. The penetration of the tip into the tissue can be observed via an optical system installed in the trocar. Since the rounded tip of the trocar is not suitable for penetration of the tissue, sharp edges are mounted in the tip which can be moved distally forward beyond the rounded, transparent trocar tip in order to separate the tissue to be penetrated. This produces the disadvantage that in the actual penetration possible by means of the distally extended cutting edges, no observation is possible.

The objective of the invention is to provide a medical needle that has a sharp, penetrating tip in which the risk of injury to vessels and organs by the sharp, penetrating tip is as low as possible.

The surgical needle herein disclosed has a sharp, penetrating tip with a protective element that can be shifted by spring actions whose distal, blunt protective surface is rounded and is optically transparent An optical system is installed in this protective element by which the protective surface can be observed from the inside.

The optical system is mounted in the protective element such that the distal lens of the system is at a distance axially from the transparent protective surface so that a good optical image of the tissue parts lying on the protective surface results. The optical system can be fixed in the protective element or mounted so that it can be changed in the protective element. An exchange mounting has the advantage that the needle can be constructed as a disposable instrument whereas the expensive optical system can be used several times. Also in the case of the disposable instrument, the exchangeability of the optical system may be of advantage because the optical system can be taken out for sterilization of the needle, and must not be exposed to the high sterilization temperatures The blunt protective surface shields the sharp tip in the distally shifted position of the protective element as well as possible, because the sharp, penetrating tip lies on the cylindrical casing surface of the protective element so that the tip does not project freely in spite of the rounding of the protective surface.

The shapes of the blunt protective surface of the protective element can be made different according to the requirements of different uses. A flat protective surface arched slightly forward provides larger surface bearing on the tissue so that a greater tissue pressure, working against the force of the spring, is exerted on the protective element.

The effect of the changing tissue resistance exploited in the conventional Veres needle can also be used in this constructed.

A more intense arching of the protective surface forward with a smaller curve radius may be advantageous from other perspectives. The smaller curve radius and more intense arching of the protective surface result in lower counterpressure of the tissue on the protective surface and the protective element in the penetration process. The lower pressure of the protective surface on the tissue has the consequence that the tissue becomes less anemic, that is, that the blood is less pressed out of the tissue, in which case the tissue would appear pale. Furthermore, the protective element with the blunt protective surface arched forward can also be intentionally pressed forward and held in the forward position in order to probe forward with the tip in the tissue while viewing, and the sharp, penetrating tip can then be used, with release of the protective element, only when it is assured that the penetration will be without danger.

During the penetration and insertion of the needle, the subdermal fatty tissue first appears yellow When the fascia is reached, it appears white. After penetration of the fascia, the muscle tissue appears red Any vessels lying in front of the tip of the needle can be recognized and avoided. If the preperitoneal fatty tissue is reached, the protective element with the blunt protective surface can intentionally be pressed forward so that the blunt protective surface, independent of the force of the spring, can be kept projecting beyond the sharp tip. The fatty tissue can be penetrated with the blunt protective surface until the protective surface contacts the wall of the peritoneum. The latter can be pressed in with the blunt protective surface without penetration, and stretched (tenting effect). In this way, the peritoneum becomes semitransparent and intestinal loops or vessels adhering to the peritoneum can be recognized.

When it can be assured in this manner that no adhesions are present beneath the peritoneum, the protective element can be released so that it recedes back behind the sharps penetrating tip. The sharp tip then penetrates the peritoneum without risk.

BRIEF DESCRIPTION OF THE DRAWINGS

FIG. 1 is an elevational view of a needle in accordance with the present invention having a protective element in the rear position, FIG. 2, the needle with the protective element in the forward position, FIG. 3 is a enlarged side view of the distal tip of the needle in the rear position of the protective element, FIG. 4 is similar to FIG. 3, rotated 90°, FIG. 5 is similar to FIG. 3, with a protective element in the forward position, and FIG. 6 is similar to FIG. 5 rotated 90°.

DESCRIPTION OF THE PREFERRED EMBODIMENT

The medical needle shown herein is constructed particularly for endoscopic surgery, for the first penetration to introduce pneumoperitoneum.

The medical needle of the present invention has outer, hollow cannula tube 10 of steel that has an outer diameter of, for example, 1.5–3 mm. The distal or forward end of cannula tube 10 is ground oblique, so that a sharp tip 12 is formed which serves for penetration of the tissue, Cannula tube 10 has, depending on the particular purpose, a length of approximately 80–150 mm.

Protective element 14 is mounted in cannula tube 10 so that it can shift axially. Protective element 14 is a tube mounted coaxially in cannula tube 10, and is closed at its distal front end. The closed distal end of protective element 14 forms a front, blunt protective surface 16 which extends forward from the casing surface of protective element 14 and has a front face, on the distal end, which is rounded.

The distal end of protective element 14 provided with protective surface 16 is optically transparent and is of glass or a transparent plastic. For this, either the entire tubular protective element 14 may be of glass or plastic, or the front end made of glass or plastic, may be mounted on a metallic tube. The axial length of the transparent, distal end of protective element 14 preferably is at least 5 mm, The transparent end of protective element 14 provided with protective surface 16 is also hollow, and inner hollow cavity 17 is shaped like a dome, that is, is sharp or rounded towards the front.

Into tubular protective element 14, from its proximal end, rod-shaped optical system 18, for example, a rod lens system, is introduced. Optical system 16 is pushed into protective element 14 until distal lens 20 of system 10 is located at an axial distance behind the distal end of protective surface 16 and internal hollow cavity 17 of protective surface 16. Optical system 18 rests in this position in protective element 14 so that it is held axially rigid in protective element 14 and moves with it when protective element 14 is shifted axially.

Protective element 14 is mounted in external cannula tube 10 and is urged by a spring arranged at the proximal end. The spring urges protective element 14 axially forward, with a predetermined spring force, into the position indicated in FIGS. 2, 5, and 6, in which protective surface 16 of protective element 14 projects beyond sharp tip 12 of cannula tube 10.

The forward movement of protective element 14 is limited such that in the final distal position thereof that is indicated in FIGS. 5 and 6 tip 12 lies in the area in which curved protective surface 16 makes a transition into the cylindrical external casing surface of protective element 14. In this way, sharp tip 12 lies close against the casing of protective element 14 and is shielded by it.

Protective element 14 can be shifted axially backwards into a rear terminal position against the force of the spring, in which protective surface 16 is pushed back behind sharp tip 12 of cannula tube 10 as shown in FIGS. 1, 3, and 4. In this rear terminal position of protective element 14, sharp tip 12 projects freely forward and can penetrate the tissue unhindered by protective surface 16.

Cannula tube 10, as shown in FIGS. 1 and 2 has handle 22 on its rear, proximal end. Protective element 14 can be mounted on headpiece 24, with its rear, proximal end at headpiece 24. Headpiece 24 has eyepiece 26 on its proximal end through which protective surface 16 can be observed by means of optical system 18. Furthermore, headpiece 24 has lateral connection 28 to which a light source and possibly a camera or image converter can be connected to optical system 18.

Valve cock 30 is provided on handle 22 through which $CO_2$ gas is delivered and can be directed to the tip through cannula tube 10 or a channel mounted in cannula tube 10, in order to insufflate the abdominal cavity When the needle is penetrating, cannula tube 10 is guided with handle 22. Headpiece 24 with protective element 14 shifts with respect to cannula tube 10. In front of headpiece 24 is lever 32 with which optical system 18 in protective element 14 can be stopped.

During penetration of the tissue, protective element 14 shifts into the front position shown in FIGS. 5 and 6 or is pressed back into the rear position indicated in FIGS. 3 and 4, depending on whether the pressure exercised on protective surface 16 due to the resistance of the penetrated tissue is less than or greater than the spring force acting on protective element 14 Optical system 18 is axially fixed in protective element 14 and moves with it when protective element 14 is shifted axially. Thus, lens 20 is always located at a predetermined axial distance from the distal end of protective surface 16 so that an optimum optical observation of the tissue lying against protective surface 16 is possible through inner hollow cavity 17 of protective surface 16.

In the embodiment disclosed cannula tube 10 is guided with handle 22 when the needle is penetrating. Because headpiece 24 shifts axially with protective element 14 in relation to the cannula tube 10, the relatively heavy headpiece cannot be held by the operator when the needle is penetrating, and generates a tipping force on the needle that can impair the guidance of the needle.

In another embodiment, therefore, optical system 18 can be shifted axially in protective element 14. In this embodiment, cannula tube 10 is fastened to headpiece 24. When the needle penetrates, cannula tube 10 and the headpiece 24 connected with it can be guided by the hand of the operator so that the weight of headpiece 24 does not have a disturbing effect. Protective element 14 shifts axially depending on the counterpressure of the tissue in relation to cannula tube 10 and also in relation to optical system 18. Thus, the axial distance between protective surface 16 and lens 20 of optical system 18 changes. Through a suitable construction of the optical system and particularly of lens 20, it can be assured that this change of distance does not to any considerable degree impair the observation of protective surface 16 through optical system 18.

We claim:

1. Medical needle with a cannula tube whose distal end is cut obliquely to a sharp tip, with a coaxially mounted tubular protective element in the cannula tube which can be moved axially from a forward position against a spring force into a rear position and which is closed at its distal end by a transparent, blunt protective surface that projects in the forward position distally beyond the tip and in the rear position is behind the tip, and an optical system in the protective element having a distal lens for observation of the protective surface from the inside, characterized by the fact that the protective surface is arched forward at its distal end, that the protective element is hollow up to the arched area of the protective surface there being inside the protective surface a dome-shaped interior hollow cavity, the lens of the optical system inside the protective element being at an axial distance from the protective surface, and in the distal, front position of the protective element, the tip of the cannula tube lies in an area in which the arched protective surface makes a transition into the cylindrical, external casing surface of the protective element.

2. A medical needle according to claim 1, wherein said optical system is removably positioned in the protective element so that it can be readily removed for use with another medical needle.

3. A medical needle according to claim 2, wherein the optical system is held in the protective element for axial movement with the protective element.

4. A medical needle according to claim 2, wherein a headpiece is connected to said cannula tube, the optical system being axially shiftable in the protective element and fastened, together with the cannula tube to said headpiece.

5. A medical needle according to claim 1, wherein the distal lens of the optical system is located approximately in the base of the dome-shaped interior hollow cavity.

6. A medical needle comprising:
   a cannula tube having a distal end with a sharp tip,
   a tubular protective element in said cannula tube axially movable from a distal forward position against a spring to a rear position,
   said tubular protective element being closed at its distal end by a transparent, blunt protective surface which in the forward position thereof projects beyond said sharp tip and which is behind the sharp tip in the rear portion thereof,
   said protective surface being arched forward at its distal end,
   said tubular protective element being configured to receive an optical system therein, and being hollow rearwardly of said arched distal end and providing a dome-shaped hollow cavity adapted to be viewed through an optical system in said tubular protective element.

7. The medical needle of claim 6, and further comprising an optical system in said tubular protective element positioned to view said dome-shaped hollow cavity of said distal end of said tubular protective element.

8. The medical needle of claim 7, said optical system comprising a lens positioned in the base of said dome-shaped hollow cavity.

9. The medical needle of claim 7, said optical system being held in said protective element for axial movement therewith.

10. The medical needle of claim 9, wherein said optical system is releasably held in said protective element.

11. The medical needle of claim 7, and further comprising a headpiece remote from said sharp point, and wherein said optical system and said headpiece are fastened for conjoint movement.

12. The medical needle of claim 11, and one of said cannula tube and said tubular protective element fastened to said headpiece for conjoint movement therewith.

13. The medical needle of claim 6, said tubular protective element having a cylindrical exterior with a transition zone to said arched protective surface, the tip of said cannula tube being at said transition zone of said tubular protective element when said tubular protective element is in the forward position thereof.

14. A medical needle comprising:
   a cannula tube having a distal end with a sharp tip,
   a tubular protective element in said cannula tube axially movable from a distal forward position against a spring to a rear position,
   said tubular protective element being closed at its distal end by a transparent, blunt protective surface which in the forward position thereof projects beyond said sharp tip and which is behind the sharp tip in the rear portion thereof,
   said protective surface being arched forward at its distal end,
   said tubular protective element being configured to receive an optical system therein, and being hollow rearwardly of said arched distal end and providing a dome-shaped hollow cavity adapted to be viewed through an optical system in said tubular protective element, said tubular protective element being configured to receive an optical system therein, said tubular protective element having a cylindrical exterior with a transition zone to said arched protective surface, the tip of said cannula tube being at said transition zone of said tubular protective element when said tubular protective element is in the forward position thereof.

15. The medical needle of claim 14, and further comprising an optical system in said tubular element positioned to view said transparent, arched surface at the distal end of said tubular protective element.

16. The medical needle of claim 15, said optical system comprising a lens positioned in the base of said dome-shaped hollow cavity.

17. The medical needle of claim 15, said optical system being held in said protective element for axial movement therewith.

18. The medical needle of claim 17, wherein said optical system is releasably held in said protective element.

19. The medical needle of claim 15, and further comprising a headpiece remote from said sharp point, and wherein said optical system and said headpiece are fastened for conjoint movement.

20. The medical needle of claim 19, and one of said cannula tube and said tubular protective element fastened to said headpiece for conjoint movement therewith.

* * * * *